United States Patent
Eskilsson et al.

(10) Patent No.: US 10,416,725 B2
(45) Date of Patent: Sep. 17, 2019

(54) WEARABLE DEVICE HAVING A DISPLAY, LENS, ILLUMINATOR, AND IMAGE SENSOR

(71) Applicant: TOBII AB, Danderyd (SE)

(72) Inventors: Henrik Eskilsson, Danderyd (SE); Mårten Skogö, Danderyd (SE)

(73) Assignee: Tobii AB, Danderyd (SE)

( * ) Notice: Subject to any disclaimer, the term of this patent is extended or adjusted under 35 U.S.C. 154(b) by 53 days.

(21) Appl. No.: 15/661,983

(22) Filed: Jul. 27, 2017

(65) Prior Publication Data

US 2018/0032103 A1 Feb. 1, 2018

Related U.S. Application Data

(60) Provisional application No. 62/367,442, filed on Jul. 27, 2016.

(51) Int. Cl.
*G06F 1/16* (2006.01)
*G06F 3/01* (2006.01)
*A61B 3/113* (2006.01)

(52) U.S. Cl.
CPC ............. *G06F 1/166* (2013.01); *A61B 3/113* (2013.01); *G06F 1/163* (2013.01); *G06F 1/1637* (2013.01); *G06F 3/011* (2013.01); *G06F 3/013* (2013.01)

(58) Field of Classification Search
None
See application file for complete search history.

(56) References Cited

U.S. PATENT DOCUMENTS

| | | | |
|---|---|---|---|
| 2005/0053274 A1* | 3/2005 | Mayer | G03B 21/18 382/154 |
| 2013/0050833 A1* | 2/2013 | Lewis | G06K 9/00604 359/630 |
| 2013/0083011 A1* | 4/2013 | Geisner | G09G 5/00 345/419 |
| 2014/0132485 A1 | 5/2014 | Kim et al. | |
| 2015/0061996 A1 | 3/2015 | Engwall et al. | |

(Continued)

OTHER PUBLICATIONS

Hillaire, et al.; "Using an Eye-Tracking System to Improve Camera Motions and Depth-of-Field Blur Effects in Virtual Environments"; 2008; 4 pages.

(Continued)

*Primary Examiner* — Joseph R Haley
*Assistant Examiner* — Emily J Frank
(74) *Attorney, Agent, or Firm* — Kilpatrick Townsend & Stockton LLP

(57) ABSTRACT

A wearable device is disclosed. The wearable device may include a display, a lens, an illuminator, an image sensor, and at least one processor. The display may be configured to present images. The lens may be configured to provide a view of the display to an eye of a user. The illuminator may be configured to illuminate the eye. The image sensor may be configured to detect illumination reflected by the eye. The at least one processor may be configured to cause the display to present an image, receive data from the image sensor, determine a gaze direction of the eye based at least in part on the data from the image sensor, and cause at least one of the display or the lens to be moved until the gaze direction is directed toward the image.

20 Claims, 4 Drawing Sheets

(56) References Cited

U.S. PATENT DOCUMENTS

2015/0062322 A1   3/2015  Andersson et al.
2015/0185503 A1*  7/2015  Tate ........................ G06F 3/013
                                                            351/158
2017/0205877 A1*  7/2017  Qin ......................... G02B 27/01

OTHER PUBLICATIONS

Guestrin, et al.; "General Theory of Remote Gaze Estimation Using the Pupil Center and Corneal Reflections"; *IEEE Transactions on Biomedical Engineering;* Jun. 2006; vol. 53, No. 6, pp. 1124-1133.
Littlewort-Ford, et al.; "Are Your Eyes Smiling? Detecting Genuine Smiles with Support Vector Machines and Gabor Wavelets"; *Proceedings of the 8th Joint Symposium on Neural Computation;* 2001; 9 pages.
Daugman; "High Confidence Visual Recognition of Persons by a Test of Statistical Independence"; *IEEE Transactions on Pattern Analysis and Machine Intelligence,* vol. 15, No. 1, 1993; pp. 1148-1161.

* cited by examiner

WEARABLE DEVICE HAVING A DISPLAY, LENS, ILLUMINATOR, AND IMAGE SENSOR

CROSS-REFERENCE TO RELATED APPLICATIONS

This application claims priority to U.S. Provisional Patent Application No. 62/367,442, filed Jul. 27, 2016, the entire contents of which are hereby incorporated by reference, for all purposes, as if fully set forth herein.

BRIEF SUMMARY OF THE INVENTION

In one embodiment, a wearable device is provided. The wearable device may include a display, a lens, an illuminator, an image sensor, and at least one processor. The display may be configured to present images. The lens may be configured to provide a view of the display to an eye of a user. The illuminator may be configured to illuminate the eye. The image sensor may be configured to detect illumination reflected by the eye. The at least one processor may be configured to cause the display to present an image, receive data from the image sensor, determine a gaze direction of the eye based at least in part on the data from the image sensor, and cause at least one of the display or the lens to be moved until the gaze direction is directed toward the image.

In another embodiment, a method for displaying images to a user is provided. The method may include causing a display to present an image through a lens to an eye of a user. The method may also include causing an illuminator to illuminate the eye of the user. The method may further include receiving data from an image sensor detecting illumination reflected by the eye. The method may additionally include determining a gaze direction of the eye based at least in part on the data from the image sensor. The method may moreover include causing at least one of the display or the lens to be moved until the gaze direction is directed toward the image.

In another embodiment, a non-transitory machine readable medium having instructions stored thereon for displaying images to a user is provided. The instructions may be executable by one or more processors to cause the one or more processors to perform a method. The method may include causing a display in a wearable device to present an image through a lens to an eye of a user. The method may also include causing an illuminator to illuminate the eye of the user. The method may further include receiving data from an image sensor detecting illumination reflected by the eye. The method may additionally include determining a gaze direction of the eye based at least in part on the data from the image sensor. The method may moreover include causing at least one of the display or the lens to be moved until the gaze direction is directed toward the image.

BRIEF DESCRIPTION OF THE DRAWINGS

Embodiments of the present invention are described in conjunction with the appended figures.

Figure 1:
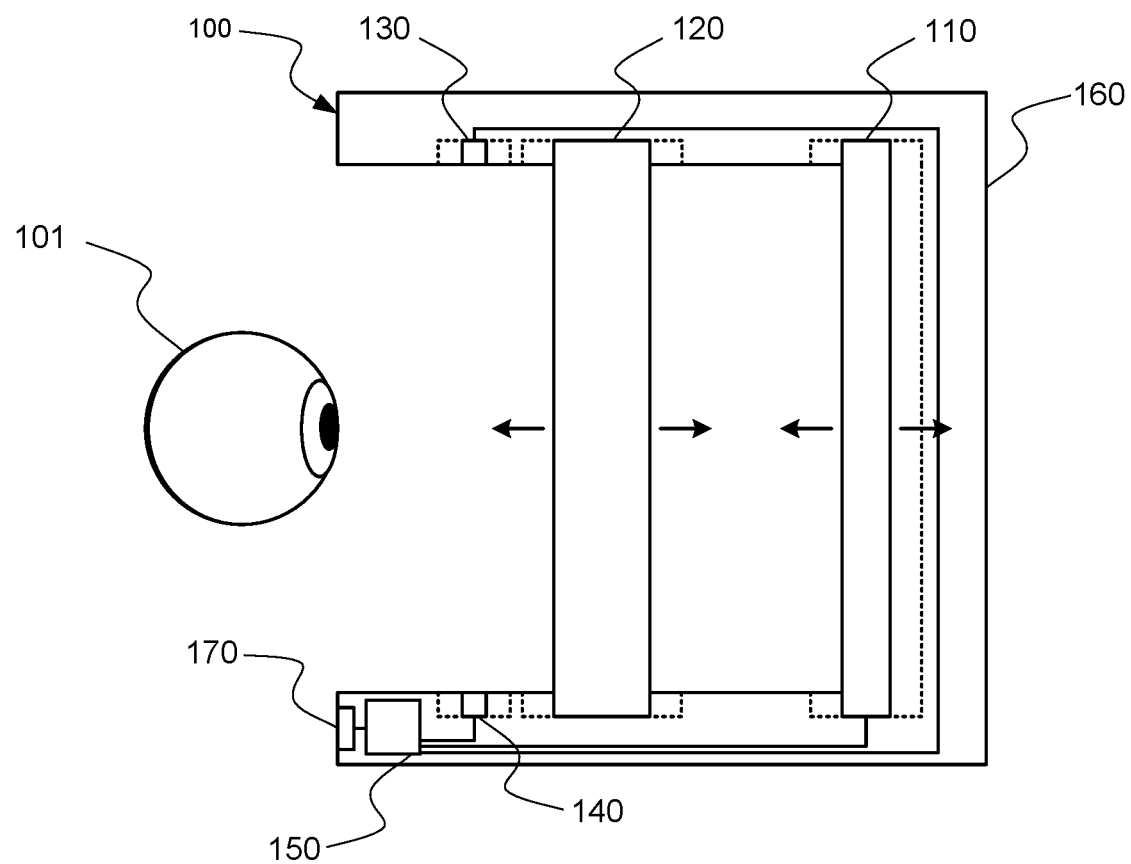
FIG. 1 is schematic diagram of a wearable device of one embodiment of the invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Wearable devices containing displays are well known, typically they are utilized in Virtual Reality (VR) and Augmented Reality (AR) systems. In these systems the displays are used to provide a user with an experience that simulates either a different reality in the case of VR, or an enhanced reality in the case of AR.

In some cases the wearable device need not contain a display of any sort, for example a system the subject of U.S. Pat. No. 9,041,787 does not require a display. The entire contents of the aforementioned patent is hereby incorporated by reference, for all purposes, as if fully set forth herein.

It has been previously proposed that the use of eye tracking devices and the like can be incorporated with these wearable devices in order to improve their performance.

Wearable eye trackers are also well known, see for example U.S. Patent Application Publication Number 2015/0062322 which describes a wearable eye tracking device. The entire contents of the aforementioned application is hereby incorporated by reference, for all purposes, as if fully set forth herein.

One implementation of eye tracking in a virtual reality device is described in *Using an Eye-Tracking System to Improve Camera Motions and Depth-of-Field Blur Effects in Virtual Environments*, Hillaire et al, 2008, Virtual Reality Conference, whereby eye tracking is used to determine a user's focus point in a virtual embodiment. The focus point is then used when rendering the virtual environment in order to improve the user's sensation when navigating the virtual environment. The entire contents of the aforementioned publication is hereby incorporated by reference, for all purposes, as if fully set forth herein.

Further, it is known that in a wearable display such as a Virtual Reality headset, certain vision conditions can affect how well a user can view the display or displays in the headset. Conditions such as farsightedness and nearsightedness which relate to how light is focused onto the retina as it enters the eye and can mean that a user either sees things well nearer to the eye and blurrier further out (nearsightedness), or sees things well further out from the eye and blurrier closer to the eye (farsightedness). Nearsightedness is otherwise known as myopia, while farsightedness is otherwise known as hypermetropia or hyperopia.

To solve this problem in wearable device containing at least one display, it has been previously proposed to provide a manual adjustment mechanism, such as a knob which when turned moves the display or displays closer to, or away from, a user's eyes. The problem with this solution is that it relies on user input to physically move the display(s), thus adding a step which may take away from the experience of wearing the device as well as provide sub-optimal correction of the display location due to user error.

A further solution previously proposed is to accommodate a user's existing eye correction lenses, such as eye glasses, inside the wearable device. This is a suboptimal solution however as it adversely impacts the fit of the wearable device, and may cause comfort issues for some users. A solution that allows for a user to wear the device without eye correction lenses is desirable.

Accordingly it is advantageous if an automatic method for correcting the display location to account for farsightedness or near-sightedness can be found.

The present invention seeks to provide improved solutions for eye tracking in wearable devices, and improved uses of eye tracking information in VR, AR or other environments. These improvements relate to hardware solutions for use in wearable devices as well as software solutions for use with wearable devices.

The present invention generally relates to a wearable device comprising a display and an image sensor, the wearable device uses information obtained through the image sensor to alter information on the display. In particular the present invention relates to systems and methods for utilizing information regarding an eye in altering information on a display.

Thus, an object of the present invention is to provide improved wearable eye tracking systems. This and other objects of the present invention will be made apparent from the specification and claims together with appended drawings.

Various embodiments and aspects of the present invention will be arranged using headings, so as to facilitate more easy understanding of the present invention.

According to a first aspect of the present invention, there is provided a wearable device comprising a display and an eye tracking apparatus. Information from the eye tracking apparatus effects items displayed on the display.

Preferably the eye tracking apparatus comprises at least one image sensor and at least one illumination source. In some embodiments the eye tracking apparatus may include two image sensors and two illumination sources. The illumination source projects illumination on the eye of a wearer of the wearable device and the image sensor captures images of the eye. Based on the location of reflection of illumination on the eye, a direction of the user's gaze may be determined. By way of example, a suitable system for determining the gaze direction of a user with a wearable eye tracking apparatus is described in U.S. Patent Application Number 2015/0061996. The entire contents of the aforementioned application is hereby incorporated by reference, for all purposes, as if fully set forth herein.

Connected directly or wirelessly to the eye tracking apparatus and display is a computing unit. The computing unit performs calculations based on information from the eye tracking apparatus and controls information displayed on the display.

Compensation for Eye Conditions

In one embodiment of the present invention, a wearable device having at least one display, at least one lens associated with the display and at least gaze measuring device provided. The device contains an automated means for moving the position of the display and/or lens, such that when the device is worn by a user, the display and/or lens can be located closer to, or farther from, a user's eyes. In some embodiments the display remains stationary, while the lens moves, or vice-versa: the lens remains stationary while the display moves. It is intended that according to this invention, any movement of a display or lens is possible.

In some embodiments, one display and lens per eye may be utilized in which case each display and/or lens may be moved independently of the other.

The gaze measuring device is utilized to determine the direction of a user's gaze, as is described elsewhere in this document and would be well known to a person skilled in the art.

In use, the display displays a sequence of images while the automated means moves the display and/or lens closer to or further from a user's eyes.

By way of example, the gaze measuring device may contain an image sensor and a processing unit, the processing unit connected to the image sensor processes images captured by the image sensor to determine if a user's gaze is fixating on any portion of the images displayed on the display. To achieve this, a series of at least one image is displayed to the user, if the image is perceived as out of focus by the user, the user's gaze pattern will not fixate on the image. If it is perceived as in-focus, the user's gaze pattern will fixate on a portion of the image. In this manner, when a user's gaze fixates upon a portion of a displayed image, the automated means can stop moving the display and the location of the display become fixed.

The displayed images may be any manner of pattern or image, including but not limited to horizontal lines, vertical lines, shapes and the like. By way of example, patterns from so-called "teller acuity cards" may be suitable for this embodiment of the present invention, these patterns comprise a high contrast black and white pattern of stripes known as a "grating" and comprise patterns having stripes of various widths. These patterns can be shaped to form images easily recognized by a user, such as dog, cat, house, car or the like, or as simple geometric shapes.

To determine if a user's gaze is focused on a portion of an image, one possible method is to apply a wave front analysis to an image captured by the image sensor to detect aberrations on a pupil surface. Another possible method is to analyze a series of movements of a user's gaze, to determine when they cease or remain substantially still to determine if a user is focusing on a particular area.

Once the gaze measuring device has determined where the user is gazing, the automated means controls the location of the display and/or lens to fix the location in place.

This embodiment of the present invention may function with any manner of gaze measuring device, for example incorporating multiple image sensors and a plurality of infrared illumination sources, as would be understood by a person of skill in the art, and some of which is described in this document. Further, any number of displays may function with this embodiment, however two displays (one per eye) is preferable. Each display may be automated separately, or together.

In a further improvement, other items in the wearable device may be automated, such as the location of the image sensor or infrared illumination sources. These items may be adjusted based on measurements derived by the processing unit, such as inter-pupillary distance. Whereby placement of illuminators and image sensors can be adjusted to accommodate greater inter-pupillary distances, providing a larger field of view for the image sensor(s), and thus a larger portion of the population may accurately have their gaze tracked.

The gaze measuring device, although described as an example in relation to imaging based eye tracking, may equally function with any other form of eye tracking device capable of determining an approximation of a direction of a user's gaze. This includes technology such as Electrooculogram (EOG), radar, magnetic field sensor or any other form of technology as would be readily understood by a person of skill in the art.

Profile Sensor

In one embodiment of the present invention, a so-called profile sensor may be used to determine the gaze direction of a user. In this embodiment a wearable device is provided containing a profile sensor directed towards at least one of a user's eyes. An example of a suitable profile sensor is that manufactured by Hammamatsu with model number S9132. The method of function of a profile will be readily understood by one of skill in the art, a profile sensor operates by summarizing the values of all pixels in a row and/or a column into a single value.

In addition at least one infrared light emitter is provided and directed towards the at least one of the user's eyes. A profile sensor in this manner may be used to determine the location of a reflection of the infrared light from the user's cornea, otherwise referred to as a 'glint'. Rudimentary gaze tracking may thus be performed by analyzing the location of the glint on the user's cornea, as would be readily understood by one of skill in the art. In a further improvement, two or more profile sensors may be used. This offers several advantages:

Firstly if more than one two dimensional profile sensor is used it is possible to determine the cornea center of a user's eye in three dimensions—after determining the corneal radius, and glint positions in three dimensions as opposed to two dimensions.

Secondly, by arranging at least two profile sensors such that resulting glints do not overlap will allow for more accurate glint detection. For example consider a case with two glints A and B. If they are imaged by a 1D profile sensor aligned in the same direction as the glints, the sensor would only register a single response caused by both glints, so it would be difficult or impossible to determine whether the glint is caused by illuminator A, illuminator B, or both illuminators. Always aligning the illuminators and profile sensors in such a way that they won't cause glints to overlap in any readout of any profile sensor would therefore be advantageous.

Alternatively illuminators may be modulated to ensure that only one illuminator is lit at any given time. A profile sensor may be designed to operate at very fast sampling rates enabling many samples, capturing a glint from one illuminator at each sample, within a short time frame to ensure only minimal eye movement between samples.

Thirdly, multiple one dimension profile sensors may be used, in order for such a system to function accurately each sensor must be placed and rotated relative to each other. In this manner the single dimension for each sensor could be alternated between being in horizontal and vertical configuration, although the relative orientation difference need not be limited to 90 degrees. Furthermore it is desirable to add a cylindrical shaped lens to each one dimension profile sensor.

According to the present invention, the profile sensor outputs the sum of all rows and/or the sum of all columns of the pixel matrix of the sensor to a processing device. A reflection of infrared light from the infrared illuminator on a user's cornea, known as a glint, is found using a technique known as peak detection. Peak detection is performed on both the sum of the rows and the sum of the columns.

In an optional improvement, in order to facilitate high speed eye tracking, where a previously calculated glint position is known—only a subset of pixels must be analyzed for a peak, for example 10-20 pixels close to the known previous glint position.

Once the glint position is known, gaze direction can be determined using, for example, a polynomial glint to gaze point model:

$$gaze_x = c_1 x + c_2 y + c_3 xy + c_4 x^2 + c_5 y^2 + c_6$$

$$gaze_y = c_7 x + c_8 y + c_9 xy + c_{10} x^2 + c_{11} y^2 + c_{12}$$

Where $gaze_x$ and $gaze_y$ are the x and y positions of the gaze point, x and y are the x and y positions of the glint and c1 . . . c12 are calibrated model parameters.

Preferably, more than one illuminator is provided in combination with the profile sensor. These illuminators may be selectively enabled or modulated, and the processing device may determine which illuminator to enable based on metrics derived from captured image data. Alternatively the illuminators may be lit in a predefined sequence ensuring that only one illuminator is lit at any given time.

In a further improvement, the wearable device further contains at least one image sensor of the conventional area sensor type. This conventional sensor is also directed to at least one of the user's eyes. The conventional sensor may capture images of a user's eye and the system may perform traditional Pupil Centre Corneal Reflection (PCCR) eye tracking, PCCR is a well-known and readily understood method of determining a user's gaze. Further information on this method can be found in multiple places, including Guestrin, E. D.; Eizenman, E., "General theory of remote gaze estimation using the pupil center and corneal reflections," *Biomedical Engineering, IEEE Transactions on*, vol. 53, no. 6, pp. 1124, 1133, June 2006. The entire contents of the aforementioned publication is hereby incorporated by reference, for all purposes, as if fully set forth herein.

By combining a profile sensor, enabled to output the sum of all columns and/or the sum of all rows, with a conventional image sensor, the system may conduct glint tracking using the profile sensor and PCCR tracking using the conventional sensor. Due to the information from the profile sensor, the conventional sensor need only run at 0.5-10 Hz. Thus the system may achieve low power consumption, low latency and a high frame (or sampling) rate.

A profile sensor tracking the glint will give good gaze data as long as the sensor stays fixed relative to the face of the user. The images from the conventional image sensor allow for slippage compensation whenever the sensor moves relative to the face. In general eye movements are substantially faster than potential slippage of a wearable device on the head of the user. It is therefore of interest to find a way of only tracking the glint position at low power and low latency. This may for instance be an enabling technology for foveated rendering in VR headsets where a relatively low power eye tracking solution can allow for substantial savings in overall power consumption of the VR system since graphics rendering can be significantly lowered.

It may for instance be possible to set the sensor in a mode where it cycles through two or more illuminators, having only one lit per sensor exposure.

For instance the sensor may be set to run a cycle where at first a first illuminator is lit during a first sensor exposure and then the sum of at least 10% of the pixel elements in at least 10% of the rows of the sensitive area and the sum of at least 10% of the pixel elements in at least 10% of the columns of the sensitive area are calculated (and a glint position is detected). Thereafter a second illuminator is lit during a second sensor exposure and then the sum of at least 10% of the pixel elements in at least 10% of the rows of the sensitive area and the sum of at least 10% of the pixel elements in at least 10% of the columns of the sensitive area are calculated. Thereafter the sensor captures a conventional image from at least a sub part of the sensitive area of the sensor while at least one of the illuminators is lit.

In an alternative implementation the sensor may be set to run a cycle where at first a first illuminator is lit during a first sensor exposure and then the sum of at least 10% of the pixel elements in at least 10% of the rows of the sensitive area are calculated. Secondly a first illuminator is lit during a second sensor exposure and the sum of at least 10% of the pixel elements in at least 10% of the columns of the sensitive area calculated. Thereafter the sensor captures a conventional image from at least a sub part of the sensitive area of the sensor while at least one of the illuminators is lit.

An image sensor enabled to operate as a conventional image sensor, but also enabled to output profiles for the sum of pixel lines and/or the sum of pixel columns of the sensitive area may preferably include output pins for synchronizing the exposure of one or multiple illuminators with the sensor exposure.

An image sensor enabled to operate as a conventional image sensor, but also enabled to output profiles for the sum of pixel lines and/or the sum of pixel columns of the sensitive area may support daisy chaining, thus allowing two or more sensors to connect to a processing unit through the same data bus, such as for instance a MIPI CSI-2 interface.

An image sensor enabled to operate as a conventional image sensor, but also enabled to output profiles for the sum of pixel lines and/or the sum of pixel columns of the sensitive area may include means for detecting the distance to an object in its field of view. This may be done through time-of-flight To compensate for ambient light profile data and/or conventional image data may from time to time be sampled without active illumination, i.e., without having any of the illuminators lit.

The image sensor may preferably be used to also identify the user through iris recognition.

An image sensor enabled to operate as a conventional image sensor, but also enabled to output profiles for the sum of pixel lines and/or the sum of pixel columns of the sensitive area may be designed so that that each pixel can only be included in the sum of columns or the sum of lines when the sensor is operated in profile mode. For instance the pixel elements may be laid out in a checker pattern where only every other pixel may be summed into a row profile and the other pixels may be summed into a column profile.

An alternative implementation of the image sensor is to have the sensitive area split into a checker pattern where every other pixel is read out in rows and every other pixel is read out in columns, essentially having an AD converter next to each row and an AD converter next to each column. This means that the conventional image for this sensor in reality would be two images at half the sensor resolution, one read out vertically and one read out horizontally. This adds a bit of computational complexity for the traditional PCCR eye tracking. The benefit would be that the sensor could be designed in such a way that it supports horizontal pixel binning for the image read out from each line and vertical pixel binning for the image read out from each column thus facilitation low power glint detection. For instance the sensor could be designed to sum of the values from 8-16 pixel elements or even more into one value, meaning that it could operate as a profile sensor supporting sub-windowing functionality, which facilitates suppression of irrelevant signals and lowers noise.

A sensor enabled to operate as a profile sensor, with or without support for sub-windowing, may preferable include hardware logic for detecting the center of the glint, thereby further reducing power consumption and the amount of data required to send to an external processing unit. In the case that the sensor supports sub-windowing it is further preferred to, after glint center detection, have the sensor change the sub-window position to ensure that a following profile image includes the glint.

An alternative implementation of an eye tracker supporting both traditional PCCR eye tracking as well as glint tracking to allow for low power eye tracking at latency and data rates supporting foveated rendering is to have a regular sensor for imaging of the eye but include hardware logic for glint center detection when the sensor operates in a certain predefined sub-window mode. This may for instance only be possible with a sub-window of 24×24 pixels, 32×32 pixels, 48×24 pixels or some other appropriate resolution.

Looking at recent advances in VR headsets OLED displays have started to appear. OLED displays are usually transparent and a mirror is placed behind them to ensure that all light is sent out forward. For eye tracking purposes it may be preferable to have a cold mirror behind an OLED display essentially reflecting all visible light from the display towards the eye of the user but letting through near-infrared (NIR) light. Thereby an eye tracking sensor detecting NIR light can be placed behind the display looking though it and thereby getting a very good view angle towards the eye of the user.

In VR headsets it is also common to use Fresnel lenses to make the display appear at further distance from the user than it in reality is. The drawback of having a lens like this is that it distorts the image from the display and likewise it will distort the image of the eye as seen from an eye tracking sensor looking through the lens. It is therefore preferable to compensate for this distortion in the eye tracking algorithms.

An additional effect of the Fresnel lens is that it may cause circular defects in the image of the eye as seen from the eye tracking sensor. The pattern is similar to the distorting effect of waves on water when you throw in a small stone and try to look at something below the surface. It is therefore preferable to calibrate an eye tracking sensor viewing an eye through a Fresnel lens to ensure that the images from the sensor are compensated for the defects of the Fresnel lens before machine vision algorithms try to detect different eye features or glints.

An image sensor enabled to operate as a conventional image sensor, but also enabled to output profiles for the sum of pixel lines and/or the sum of pixel columns of the sensitive area may be designed to support sub-windowing. This is common in conventional image sensors, but by allowing sub-windowing when operated in profile mode much of the potentially disturbing reflections or light sources in the field of view from the sensor may be removed already before the pixel elements are summed up to a row profile and/or column profile, thus ensuring higher accuracy in the glint position determination and allowing for re-centering of the sub-window for subsequent sample.

Masking Light

Another embodiment of the present invention allows for the use of hardware or software to perform mathematical operations along lines across a 2D image sensor to provide output similar to that of a profile sensor. The lines would typically be the rows and columns of that sensor, but won't necessarily have to be limited to those orientations. This would allow other operations than just the mean and/or sum of all pixel values on a line to be calculated, as well as making it possible to mask light contribution from parts of the image known not to contain any glints. Masking light contribution from parts of the image not containing any glints increases the signal to noise ratio, and hence aids in detection of the glint by allowing examination of the intensity profile of a profile response. The preferred area to mask would in many cases be everything outside the cornea, and the most recent output from the eye tracking algorithms could be used to give an approximate area to mask.

Simulating a 2D profile sensor using a traditional image sensor reduces the computational load required for eye tracking and hence power consumption, framerate however is limited by the to the framerate of the 2D imaging sensors.

It is possible to mask light contribution from parts of the image not containing any glints even when using a real profile sensor.

One method to mask light from parts of the image known not to contain any glints is through the use of one or several illuminators whose light can be spatially controlled (such as an infrared OLED array behind a lens, any arrangement with a DLP or LCOS projector, or a multitude of other solutions readily understood by one skilled in the art).

Yet another way to mask light from parts of the image known not to contain any glints is through the use of elements blocking parts of the light before entering the profile sensor. Those blocking elements could be LCD based, mechanical, or based on a multitude of other solutions readily understood by one skilled in the art.

Simulating a Profile Sensor Using a Traditional Image Sensor

It is possible to utilize a traditional image sensor comprising a matrix of pixels to simulate a profile sensor. To achieve this hardware or software may perform mathematical operations (such as calculating the average intensity level along a line on the sensor or the sum of all intensity levels along a line on the sensor) to provide output similar to that of a profile sensor, typically this would equate to outputting rows or columns from the traditional sensor however it is possible to output any configuration of pixels, for example a diagonal line. By using this simulated system it is possible to perform more operations than just the traditional mean and sum of all pixel values on a line, such as masking as previously described, further it would be possible to mask detected light from areas of a captured image (pixels in the image sensor) known not to contain any glints. By performing this masking function, the signal to noise ratio would be increased. An example of an area to mask is the area outside of a user's cornea, as this area cannot contribute a glint.

The masking of light from areas of an image not contributing a glint may be performed using a traditional profile sensor. Further options for masking light include utilizing illuminators whose light may be spatially controlled, such as an infrared OLED array behind a lens, any arrangement with a DLP or LCOS projector or any other solution readily understood by a person skilled in the art. Another option is to block light from non-contributing areas from reaching the sensor, this may be achieved by a mechanical solution, LCD solution or any other solution understood by a person skilled in the art. A mechanical LCD solution may comprise placing a transparent LCD in front of a profile sensor.

Eye Tracker Synchronized with Display

For certain applications of eye tracking it is valuable to synchronize the eye tracking device with the display, particularly in a wearable device. In accordance with this aspect of the present invention, a wearable device is provided with a display, at least one camera and at least one illuminator. The at least one camera and at least one illuminator form an eye tracking device. Either the camera and/or the illuminator may be synchronized with the display. Synchronizing may be characterized as: synchronizing the camera strobe rate with the v-sync of the display.

It is further desirable to synchronize the eye tracking device with a position device or devices. For example the eye tracking device may be synchronized with an inertial measurement unit or the like, or with a room position device such as a system using infrared or other non-visible light, such a system has been proposed by Valve® under the name "Lighthouse". A person of skill in the art will readily understand how such synchronization may function.

Removable Eye Tracker

In accordance with another aspect of the present invention, a removable eye tracker is provided whereby the eye tracker may be inserted into a wearable device. Preferably the eye tracker is integrated with another device such as a phone, tablet, watch, display or the like.

The eye tracker comprises at least one camera and at least one illuminator, its primary function may be to track a user's gaze relative to the device into which it is integrated—for example a phone, tablet or watch. As a secondary function, the device into which the eye tracker is integrated may be inserted into a wearable device. The device may then provide the wearable device with functionality such as a display and the eye tracker may be used to determine the gaze direction of a wearer of the wearable device. The method of operation of the eye tracker may be any traditional method or any method described in this document.

Smile Authentication

According to one aspect of the present invention an image sensor in a wearable device used for eye tracking may also be used to capture images of an area around a user's eyes. These images may be analyzed to determine if a user is smiling and whether that smile is genuine or fake. It is known that characteristics of the areas around a user's eye can be used to determine if a smile is fake or genuine, see for example Littlewort-Ford, Gwen, Marian Stewart Bartlett, and Javier R. Movellan. "Are your eyes smiling? detecting genuine smiles with support vector machines and gabor wavelets." *Proceedings of the 8th Joint Symposium on Neural Computation.* 2001. The entire contents of the aforementioned publication is hereby incorporated by reference, for all purposes, as if fully set forth herein.

According to the present invention, an image sensor used for eye tracking captures at least a portion of the area around the eyes when capturing images of the eyes, these images may then be analysed using known smile detection algorithms to determine whether a user's smile is fake or genuine.

Calibration Based on Iris Identification

According to the present invention, an image sensor used for eye tracking further captures information relating to a user's iris. This iris can be used to determine the identity of the user for input into a system connected to the eye tracker.

For example, according to the present invention a wearable device is provided wherein at least one image sensor and at least one infrared illuminator is provided. The image sensor and illuminator faces toward an eye or eyes of a user wearing the device. Optionally, the device further contains a display such as in a Virtual Reality headset.

The image sensor captures images of the iris of the user and passes said images to a processing device, the processing device may be located on the wearable device or may be located remote from the processing device, in which case communication may be effected by wired or wireless means as would be understood by one of skill in the art.

Iris recognition is a known art, it uses mathematical pattern-recognition techniques to uniquely identify a pattern on one iris or both of a irises of a user for identification or authentication of the user. In its most basic form, iris recognition comprises the steps of:

Localization: Calculating the inner and outer boundaries of the iris.

Normalization: Normalizing the captured data for consistency.

Feature extraction: Forming a feature vector of features extracted from captured images.

Matching: Classifying the feature vector using thresholding techniques.

Many algorithms have been proposed which allow for iris recognition, see for example Daugman J. G., *High confidence visual recognition of persons by a test of statistical independence*, IEEE Transactions on Pattern Analysis and Machine Intelligence, Volume: 15, No. 1 I, (1993), pp. 1148-1 161. The entire contents of the aforementioned publication is hereby incorporated by reference, for all purposes, as if fully set forth herein.

Based on images of the user's iris, the processing unit connected (wired or wirelessly) with the wearable device may use the identification of the user to influence its function. For example when using an eye tracker, the processing unit may load a calibration profile which provides information specific to a user regarding an offset between their calculated gaze position and actual gaze position. By way of another example, the identification may be used to authenticate the user as authorised to operate the wearable device or operate the processing unit connected thereto.

Eye Torsion Compensation

According to another aspect of the present invention, it is possible to track eye torsion. By way of explanation, the human eye is attached to muscles in such a way that the eye, in addition to moving left/right and up/down, can also rotate such that the top of the iris may be rotated closer to the nose while the bottom of the iris rotates further away from the nose. The opposite rotation is of course also possible. This type of rotation is generally referred to as eye torsion.

When a human rotates their head slightly to their side, most humans automatically rotate their eyes slightly in the opposite direction, keeping their eyes close to level with the horizon. This effect is only in action during small rotations, since it's not possible to rotate the eye a large number of degrees in this way.

This phenomena introduces an additional source of errors in eye tracking systems for all persons whose fovea isn't perfectly centered along the optical axis of the eye.

The present invention may track eye torsion by watching the iris and/or other features on the eye ball and/or using orientation information from the eye tracker. This would provide the eye tracker with a better estimation of the position of the fovea, and hence would provide a better estimate of the gaze of the eye-tracked subject when their head is tilted.

Corneal Curvature

According to one embodiment of the present invention, the at least one image sensor captures images of a user's eye. The computing unit utilizes this information to determine the shape of the cornea of a user. Depending on the position and orientation of reflections from an infrared light source, the curvature of a cornea may be measured. In some people, their cornea has an abnormal curvature. This may be referred to as astigmatism.

By using information obtained from an image sensor and infrared light sources, the curvature of the cornea may be modeled and thus a user with an abnormally shaped cornea may be identified. By determining the shape of the cornea, corrective measures such as prescribing an appropriate lens may be performed.

EXEMPLARY EMBODIMENTS

Turning to FIG. 1, a block diagram of a wearable device 100 is shown. A user's eye 101 is also shown for reference. Wearable device 100 may include a display 110, a lens 120, an illuminator 130, an image sensor 140, and at least one processor 150. The aforementioned components may be provided for in a housing 160.

Processor 150 may be able to control and/or accept feedback/data from any of the aforementioned components, or other components discussed herein. In this embodiment, processor 150 is shown as an integral portion of wearable device 100, however, in other embodiments processor 150 could be located remotely from the remainder of wearable device 100. Merely by way of example, a mobile phone or device; tablet computer; wearable computer such as a smart watch; laptop computer; notebook computer; desktop computer; cloud processing device; and/or other processing device could instead provide processor 150.

In some embodiments, processor 150 may be just one processor used to implement the systems and methods described herein, and a communication interface 170 may allow for additional processors to at least assist in implementing the systems and methods described herein. A battery, power source, or power interface may also be provided to deliver power for components of wearable device 100. In embodiments where the processor 150 is included in wearable device 100, interface 170 may still be present to allow signals and/or data from processor 150 and/or other components to be transmitted to, or retrieved by, remote systems, and/or to allow a remote system to control components of wearable device 100.

Display 110 may be configured to present images, and may, merely by way of example, be provided via a Light Emitting Diode (LED) display, Liquid Crystal Display (LCD), or the like. Other types of displays may also be used, as will be recognized by those of skill in the art.

Lens 120 may be configured to provide a view of display 100 to eye 101 of a user. Lens 120 may be a Fresnel lens in some embodiments, for example virtual reality or personal display headsets. In other embodiments, such as augmented reality headsets, different types of lenses may be employed depending on the particular function or purpose of wearable device 100.

In some embodiments, the arrangement shown in FIG. 1 may be substantially duplicated for the other eye of the user. Some components, for example processor 150 and interface 170, may service both arrangements. Other components, for example display 110, lens 120, illuminator 130, and image sensor 140 may be provided in duplicate, with one or more of each component servicing a single eye. Any embodiment discussed herein may be applied to one or both eyes of a user.

Illuminator 130 may be configured to illuminate eye 101. In some embodiments, multiple illuminators 130 may service each eye, or both eyes of the user. Image sensor 140 may be configured to detect illumination reflected by eye 101. In some embodiments, multiple image sensors 140 may service each eye, or both eyes of the user. Processor 150 may be able to control and/or receive feedback/data from illuminator 130 and image sensor 140 in order to determine a gaze direction of eye 101. Likewise, in embodiments servicing both eyes of the user, an overall gaze direction of the user may be determined by processor 150. Any of the components of wearable device 100 may be located in different positions than shown in FIG. 1, as the positioning of these components therein is merely for exemplary purposes.

As discussed above, if an image on display 110 is at a distance from user at which the user is unable to focus through lens 120, processor 150 may determine that a gaze direction of eye 101 is not directed toward the image. This will be due to the user not being able to clearly discern the image, and hence the gaze direction of the user will move in a pattern not indicative of an intended focusing on the image. Therefore, this failure to maintain a gaze direction toward the image may indicate that the image on display 110 is out of focus to eye 101.

Thus, processor 150 may be configured to cause display 110 to present an image to eye 101, cause illuminator 130 to illuminate eye 101, receive data from the image sensor 140 indicative of illumination reflected by eye 101, determine a gaze direction from the data, determine that the gaze direction of the eye is not directed toward the image (i.e., because of the user's inability to focus on the image), and cause at least one of display 110 or lens 120 to be moved until the gaze direction is determined by processor 150 to be directed to the image, thereby indicating the user has achieved focused on the image.

In some embodiments, the gaze direction of the user may be required to be directed toward the image for some minimum amount of time prior to a determination being made that the user is indeed focusing on the image. Merely by way of example, such minimum amount of time may be about 0.1 seconds, about 0.5 seconds, about 1.0 seconds, about 1.5 seconds, about 2.0 seconds, or about any 0.1 second increment between the above values. Movement of display 110 and/or lens 120 may be conducted in incremental steps allowing for these time periods, or greater time periods, to elapse prior to another incremental movement of display 110 and/or lens 120. In this manner, time can be allowed for the user to focus on the image for the requisite amount of time when the user is able to do so, prior to another movement of display 110 and/or lens 120.

Figure 2:
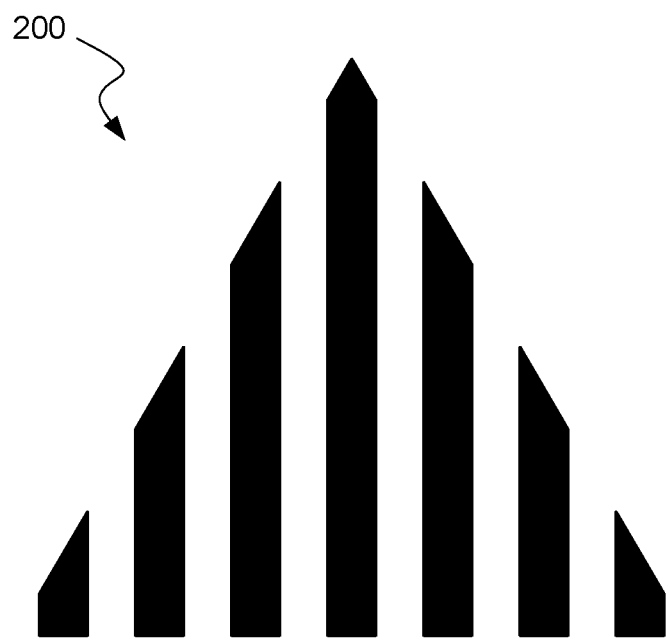
FIG. 2 is an example grated image useful in some embodiments of the invention.

In some embodiments, the image displayed may be a grated image. FIG. 2 shows one example of a grated image 200 where a geometric shape, a triangle, is defined by the image. Other shapes, including geometric shapes such as circles and squares, and non-geometric shapes such as silhouettes of animals or common consumer items such as telephones, etc., may also be used. Any image which is likely to invoke a focusing of eye 101 may be employed. Horizontal grating, as opposed to vertical grating as shown in FIG. 2, may also be employed in some embodiments.

In some embodiments, a 3D shape or object could be displayed where an embodiment provides service to both eyes of the user. In this manner, the proper distance for both display 110 and lens 120 at each eye could be determined independently.

In some embodiments, the grated image may only appear on a portion of display 110, as shown in FIG. 2. In other embodiments, the grated image may appear on all, or substantially all, of display 110. In some embodiments, remaining portions of display 110 may be presented in some level of grayscale.

In some embodiments, grated images could be provided at different grating resolutions, perhaps as the lens is moved continuously, or in steps, toward and/or away from eye 101 while the ability of the user to focus (i.e., whether the user's gaze direction is toward the image) is monitored. Merely by way of example, while the triangle of FIG. 2 may be shown in a manner such that every vertical solid black and white "grate" is 10 pixels wide, this resolution could be stepped up or down in sequential images. For example, resolution could be increased to 5 pixel wide "grates," where the number of vertical solid black and white "grates" would double, and each would be half as wide as the 10 pixel wide "grates." Resolution could be further increased to 3 pixel wide "grates," and even further to 1 pixel wide "grates." Any resolution of grating is possible.

In some embodiments, the highest resolution of grating (for example, 1 pixel grating), may first be displayed in an attempt to determine if the user can focus on such grating at any distance combinations of display 120 and lens 110. If focus is not achieved by eye 101, grating resolution may be lowered (for example, 2 pixel grating), and all distance combinations of display 120 and lens 110 may again be tried to see if the user achieves focus. Continual lowering of grating resolution may be tried until focus is achieved.

In some embodiments, processor 150 may not end the process of moving display 110 and/or lens 120 immediately upon a determination that the gaze direction is toward the image (i.e., focus has been achieved). In some embodiments, the "edges" of focus may be determined by the following process. An image with a grating of a certain resolution (for example, 5 pixel wide grating) may be displayed, and processor 150 may move display 110 and/or lens 120 to determine the longest, and shortest, effective focal distance at which the gaze direction is toward the image (i.e., the user has focused on the displayed image). Processor 150 may then increase the resolution of the image (for example, 3 pixel wide grating) on display 120, and then move display 110 and/or lens 120 to determine the longest, and shortest, effective focal distance at which the gaze direction is toward the image (i.e., the user has focused on the displayed image). The same process may then be conducted for higher and higher resolution grating (for example, 1 pixel wide grating), until an optimal midpoint effective focal distance can be determined for the highest resolution for which effective focal distance range can be determined.

Display 110 and lens 120 may possibly be moved as shown by the arrows thereat in FIG. 1 in order to focus the image displayed for the user. In other embodiments, movement of display 110 and lens 120 may also occur in the other primary axes, or some combination thereof. For example, if the arrows shown in FIG. 1 are assumed to be in the Y-axis, movement could also occur in the X-axis (left to right to the user) and Z-axis (up and down to the user).

Some embodiments may allow for both display 110 and lens 120 to be moved, while in other embodiments, only one or the other of display 110 or lens 120 may be moved. In some embodiments display 110 or lens 120 may first be moved in an attempt to achieve user focus, while the other of display 110 or lens 120 may only be moved after the first component is moved without achieving user focus. In other embodiments, both components may be moved at the same time in an attempt to achieve focus.

Movement of display 110 and/or lens 120 could be achieved through any means known in the art. Merely by way of example, one or more stepper motors fixedly located in housing 160 having a pinion gear thereon could actuate rack gears fixedly coupled with display 110 and/or lens 120. Other movement means known in the art could also be employed. FIG. 1 shows dotted lines in proximity to display 110 and lens 120 which are indicative of potential example movement ranges for these components.

In some embodiments, processor 150 may implement learning or other programmed processes which identify certain data from image sensor 140 as being indicative of certain needed corrective actions regarding movement of display 110 and lens 120. For example, certain eye/gaze movement patterns, learned over time by processor, or pre-programmed, may indicate either display 110 or lens 120 should be moved away from eye 101, while other eye/gaze movement patterns, learned over time by processor, or pre-programmed, may indicate either display 110 or lens 120 should be moved toward eye 101.

In some embodiments, illuminator 130 and image sensor 140 may also be movable by processor 150, along with any secondary lenses associated therewith. Movement of illuminator 130 and/or image sensor 140 could be achieved through any means known in the art. Merely by way of example, one or more stepper motors fixedly located in housing 160 having a pinion gear thereon could actuate rack gears fixedly coupled with illuminator 130 and/or image sensor 140. Other movement means known in the art could also be employed. FIG. 1 shows dotted lines in proximity to illuminator 130 and image sensor 140 which are indicative of potential example movement ranges for these components. In some embodiments, the functioning of secondary lenses provided for illuminator 130 and/or image sensor 140 may be provided by (primary) lens 120 and/or integrated components therewith. U.S. patent application Ser. No. 15/651,976, filed on Jul. 17, 2017, discusses such arrangements. The entire contents of the aforementioned application are hereby incorporated by reference, as if fully set forth herein.

In some embodiments, processor 150 may move illuminator 130 and/or image sensor 140 in order to increase the efficiency or ability of illuminator 130 and/or image sensor 140 to provide sufficient quality data necessary for determination of the gaze direction of eye 101. Movement of illuminator 130 and/or image sensor 140 may occur in any of the primary axes, or some combination thereof. In some embodiments, processor 150 may determine whether and how to move illuminator 130 and/or image sensor 140 based at least in part on data received from image sensor 140. For example, and especially in embodiments where both eyes are serviced, data received from image sensor 140 may allow processor 150 to determine an inter-pupillary distance which, once determined, indicates to processor that illuminator 130 and/or image sensor 140 should be relocated to increase the availability or quality of gaze direction detection for the particular user.

Figure 3:
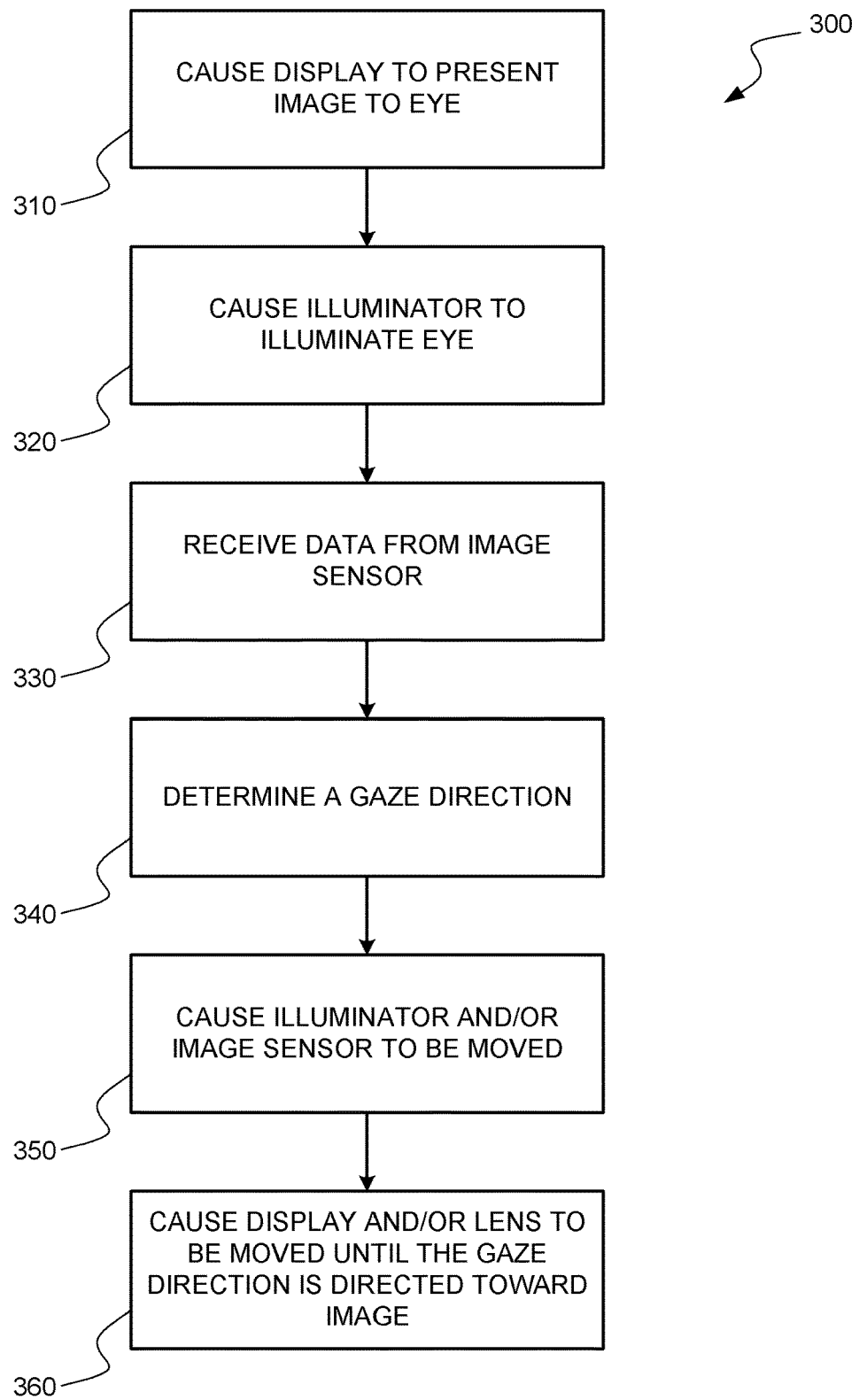
FIG. 3 is flow diagram of one method embodiment of the invention.

Turning to FIG. 3, a method 300 for displaying images to a user as described is shown. At block 310, method 300 may include causing a display to present an image through a lens to an eye of a user. At block 320, method 300 may include causing an illuminator to illuminate the eye of the user. At block 330, method 300 may include receiving data from an image sensor detecting illumination reflected by the eye. At block 340, method 300 may include determining that a gaze direction of the eye based at least in part on the data from the image sensor. At block 350, method 300 may include causing at least one of the illuminator or the image sensor to be moved. Like other steps of method 300, block 350 may occur at any other point in time during execution of method 300. At block 360, method 300 may include causing at least one of the display or the lens to be moved until the gaze direction is directed toward the image (i.e., focus has been achieved).

In another embodiment, a non-transitory machine readable medium having instructions stored thereon for displaying images to a user is provided. The instructions may be executable by one or more processors to cause the one or more processors to perform a method as discussed herein. The method may include causing a display in a wearable device to present an image through a lens to an eye of a user. The method may also include causing an illuminator to illuminate the eye of the user. The method may further include receiving data from an image sensor detecting illumination reflected by the eye. The method may additionally include determining a gaze direction of the eye based at least in part on the data from the image sensor. The method may moreover include causing at least one of the display or the lens to be moved until the gaze direction is directed toward the image. Any other steps discussed herein may also be included in the method executed by the instructions stored on the non-transitory machine readable medium.

EXEMPLARY COMPUTER SYSTEM

Figure 4:
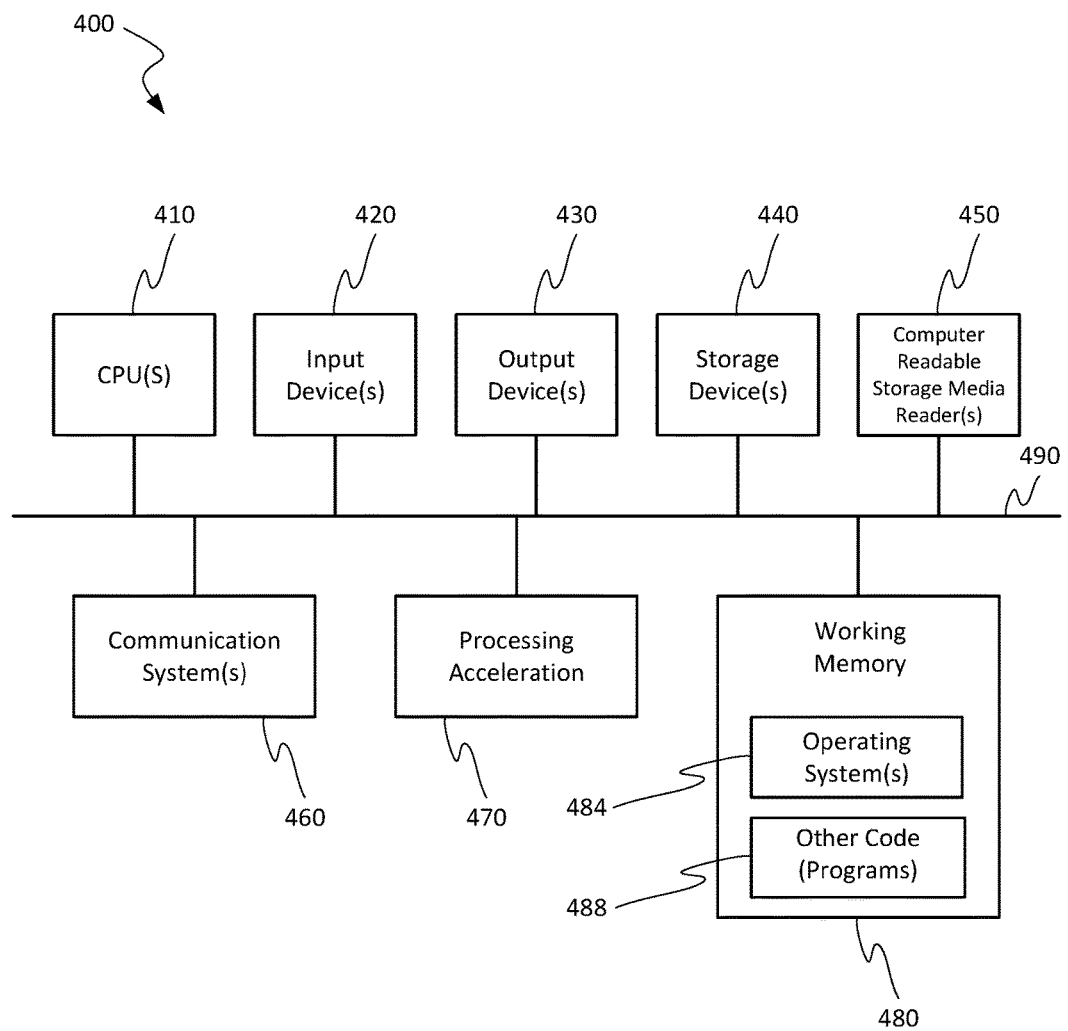
FIG. 4 is a block diagram of an exemplary computer system capable of being used in at least some portion of the apparatuses or systems of the present invention, or implementing at least some portion of the methods of the present invention.

FIG. 4 is a block diagram illustrating an exemplary computer system 400 in which any of the embodiments of the present invention may be implemented. This example illustrates a computer system 400 such as may be used, in whole, in part, or with various modifications, to provide the functions of the systems and methods described above.

The computer system 400 is shown comprising hardware elements that may be electrically coupled via a bus 490. The hardware elements may include one or more central processing units 410, one or more input devices 420 (e.g., eye-tracking device, a mouse, a keyboard, a touchpad, a microphone, etc.), and one or more output devices 430 (e.g., a display device, a printer, etc.). The computer system 400 may also include one or more storage device 440. By way of example, storage device(s) 440 may be transitory and/or non-transitory disk drives, optical storage devices, solid-state storage device such as a random access memory ("RAM") and/or a read-only memory ("ROM"), which can be programmable, flash-updateable and/or the like.

The computer system 400 may additionally include a computer-readable storage media reader 450, a communications system 460 (e.g., a modem, a network card (wireless or wired), an infra-red communication device, Bluetooth™ device, cellular communication device, etc.), and working memory 480, which may include RAM and ROM devices as described above. In some embodiments, the computer system 400 may also include a processing acceleration unit 470, which can include a digital signal processor, a special-purpose processor and/or the like.

The computer-readable storage media reader 450 can further be connected to a computer-readable storage medium, together (and, optionally, in combination with storage device(s) 440) comprehensively representing remote, local, fixed, and/or removable storage devices plus storage media for temporarily and/or more permanently containing computer-readable information. The communications system 460 may permit data to be exchanged with a network, system, computer and/or other component described above.

The computer system 400 may also comprise software elements, shown as being currently located within a working memory 480, including an operating system 484 and/or other code 488. It should be appreciated that alternate embodiments of a computer system 400 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 400 may include code 488 for implementing any or all of the function of the various elements of the architecture as described herein. For example, software, stored on and/or executed by a computer system such as system 400, can provide the functions of the methods and systems discussed above. Methods implementable by software on some of these components have been discussed above in more detail.

The invention has now been described in detail for the purposes of clarity and understanding. However, it will be appreciated that certain changes and modifications may be practiced within the scope of the appended claims.

What is claimed is:

1. A wearable device, wherein the wearable device comprises:
    a display configured to present images;
    a lens configured to provide a view of the display to an eye of a user;
    an illuminator configured to illuminate the eye;
    an image sensor configured to detect illumination reflected by the eye; and
    at least one processor configured to:
        cause the display to present an image;
        receive data from the image sensor;
        determine a gaze direction of the eye based at least in part on the data from the image sensor, the gaze direction indicative of the eye not focused on the image; and
        cause at least one of the display or the lens to be moved until the gaze direction indicates the eye is focused on the image.

2. The wearable device of claim 1, wherein:
causing at least one of the display or the lens to be moved comprises moving at least one of the display or the lens toward or away from the eye.

3. The wearable device of claim 1, wherein:
causing at least one of the display or the lens to be moved comprises causing the display to be moved.

4. The wearable device of claim 1, wherein:
causing at least one of the display or the lens to be moved comprises causing the lens to be moved.

5. The wearable device of claim 1, wherein:
causing the display to present an image comprises causing the display to present a grated image.

6. The wearable device of claim 1, wherein:
the processor is further configured to cause at least one of the illuminator or the image sensor to be moved.

7. The wearable device of claim 6, wherein:
causing at least one of the illuminator or the image sensor to be moved comprises causing the illuminator to be moved.

8. The wearable device of claim 6, wherein:
causing at least one of the illuminator or the image sensor to be moved comprises causing the image sensor to be moved.

9. The wearable device of claim 6, wherein:
the processor causes at least one of the illuminator or the image sensor to be moved based at least in part on the data received from the image sensor.

10. The wearable device of claim 9, wherein:
the processor is further configured to determine an inter-pupillary distance based at least in part on the data received from the image sensor; and
causing at least one of the illuminator or the image sensor to be moved based at least in part on data received from the image sensor comprises causing at least one of the illuminator or the image sensor to be moved based at least in part on the inter-pupillary distance.

11. A method for displaying images to a user, wherein the method comprises:
causing a display to present an image through a lens to an eye of a user;
causing an illuminator to illuminate the eye of the user;
receiving data from an image sensor detecting illumination reflected by the eye;
determining a gaze direction of the eye based at least in part on the data from the image sensor, the gaze direction indicative of the eye not focused on the image; and
causing at least one of the display or the lens to be moved until the gaze direction indicates the eye is focused on the image.

12. The method for displaying images to a user of claim 11, wherein:
causing at least one of the display or the lens to be moved comprises moving at least one of the display or the lens toward or away from the eye.

13. The method for displaying images to a user of claim 11, wherein:
causing the display to present an image comprises causing the display to present a grated image.

14. The method for displaying images to a user of claim 11, wherein the method further comprises:
causing at least one of the illuminator or the image sensor to be moved.

15. The method for displaying images to a user of claim 14, wherein:
causing at least one of the illuminator or the image sensor to be moved based is based at least in part on the data received from the image sensor.

16. A non-transitory machine readable medium having instructions stored thereon for displaying images to a user, wherein the instructions are executable by one or more processors to cause the one or more processors to at least:
cause a display in a wearable device to present an image through a lens to an eye of a user;
cause an illuminator to illuminate the eye of the user;
receive data from an image sensor detecting illumination reflected by the eye;
determine a gaze direction of the eye based at least in part on the data from the image sensor, the gaze direction indicative of the eye not focused on the image; and
cause at least one of the display or the lens to be moved until the gaze direction indicates the eye is focused on the image.

17. The non-transitory machine readable medium of claim 16, wherein:
causing at least one of the display or the lens to be moved comprises moving at least one of the display or the lens toward or away from the eye.

18. The non-transitory machine readable medium of claim 16, wherein:
causing the display to present an image comprises causing the display to present a grated image.

19. The non-transitory machine readable medium of claim 16, wherein the instructions are further executable to at least:
cause at least one of the illuminator or the image sensor to be moved.

20. The non-transitory machine readable medium of claim 19, wherein:
causing at least one of the illuminator or the image sensor to be moved based is based at least in part on the data received from the image sensor.

* * * * *